United States Patent
Verlee et al.

(10) Patent No.: US 11,446,055 B1
(45) Date of Patent: Sep. 20, 2022

(54) LIGHT ASSISTED NEEDLE PLACEMENT SYSTEM AND METHOD

(71) Applicant: Lumoptik, Inc., Washington Island, WI (US)

(72) Inventors: Donald J Verlee, Libertyville, IL (US); Thomas Janicki, Shaker Heights, OH (US)

(73) Assignee: Lumoptik, Inc., Washington Island, WI (US)

( * ) Notice: Subject to any disclaimer, the term of this patent is extended or adjusted under 35 U.S.C. 154(b) by 618 days.

(21) Appl. No.: 16/163,803

(22) Filed: Oct. 18, 2018

(51) Int. Cl.
| | | |
|---|---|---|
| *A61B 17/00* | (2006.01) | |
| *A61B 17/34* | (2006.01) | |
| *A61B 5/00* | (2006.01) | |
| *A61B 90/00* | (2016.01) | |
| *A61M 25/01* | (2006.01) | |
| *A61M 25/00* | (2006.01) | |

(52) U.S. Cl.
CPC ........ *A61B 17/3403* (2013.01); *A61B 5/0084* (2013.01); *A61B 17/3401* (2013.01); *A61B 90/06* (2016.02); *A61B 5/6848* (2013.01); *A61B 2017/00057* (2013.01); *A61B 2090/062* (2016.02); *A61M 2025/0007* (2013.01); *A61M 2025/0166* (2013.01)

(58) Field of Classification Search
CPC ... A61B 17/3403; A61B 90/06; A61B 5/0084; A61B 17/3401; A61B 2090/062; A61B 5/6848; A61B 2017/00057; A61M 2025/0007; A61M 2025/0166
See application file for complete search history.

(56) References Cited

U.S. PATENT DOCUMENTS

| | | | |
|---|---|---|---|
| 4,269,192 | A | 5/1981 | Matsuo |
| 4,867,529 | A | 9/1989 | Utsumi et al. |
| 5,116,329 | A | 5/1992 | Vannus et al. |
| 5,213,811 | A | 5/1993 | Frisbee et al. |
| 5,261,410 | A | 11/1993 | Alfano et al. |
| 5,318,528 | A | 6/1994 | Heaven et al. |
| 5,354,294 | A | 10/1994 | Chou |
| 5,396,880 | A | 3/1995 | Kagan et al. |
| 5,510,895 | A | 4/1996 | Sahagen |
| 5,534,997 | A | 7/1996 | Schrader |

(Continued)

FOREIGN PATENT DOCUMENTS

| | | |
|---|---|---|
| WO | 1989002718 | 4/1989 |
| WO | 1990012536 | 11/1990 |

(Continued)

OTHER PUBLICATIONS

Hamamatsu Photonics K.K., "Mini-spectrometer—Micro series—C12880MA", Sep. 2018, Cat. No KACC1226E09, www.hamamatsu.com.

(Continued)

*Primary Examiner* — Colin T. Sakamoto
*Assistant Examiner* — Adam D. Kolkin
(74) *Attorney, Agent, or Firm* — FisherBroyles, LLP

(57) ABSTRACT

Systems and methods to assist a practitioner to confirm location of a distal tip of a needle within a patient include confirming tactile feedback from a needle insertion to a point of loss of resistance of fluid flow and by viewing a display showing color of a tissue plane at the distal tip of the needle at the point of loss of resistance.

14 Claims, 10 Drawing Sheets

(56) References Cited

U.S. PATENT DOCUMENTS

| | | |
|---|---|---|
| 5,739,536 A | 4/1998 | Bucholtz et al. |
| 5,862,273 A | 1/1999 | Pelletier |
| 5,921,915 A | 7/1999 | Aznoian et al. |
| 5,983,125 A | 11/1999 | Alfano et al. |
| 6,006,001 A | 12/1999 | Alfano et al. |
| 6,095,982 A | 8/2000 | Richards-Kortum et al. |
| 6,366,726 B1 | 4/2002 | Wach et al. |
| 6,487,349 B2 | 11/2002 | Wach et al. |
| 6,564,087 B1 | 5/2003 | Pitris et al. |
| 7,761,139 B2 | 7/2010 | Tearney et al. |
| 7,787,129 B2 | 8/2010 | Zysk et al. |
| 2001/0012429 A1 | 8/2001 | Wach et al. |
| 2005/0027199 A1 | 2/2005 | Clarke |
| 2008/0195081 A1 | 8/2008 | Moll |
| 2009/0099501 A1 | 4/2009 | Chang et al. |
| 2009/0157044 A1 | 6/2009 | Liyanagama et al. |
| 2010/0022824 A1 | 1/2010 | Cybulski et al. |
| 2010/0256483 A1* | 10/2010 | Wall ............ A61B 1/3135 600/407 |
| 2011/0054353 A1 | 3/2011 | Hulvershorn et al. |
| 2011/0092810 A1 | 4/2011 | Trovato |
| 2011/0092823 A1 | 4/2011 | Tearney et al. |
| 2011/0230760 A1 | 9/2011 | Gambhir et al. |
| 2012/0088991 A1 | 4/2012 | Nachabe et al. |
| 2012/0259229 A1 | 10/2012 | Wang et al. |
| 2013/0018303 A1 | 1/2013 | Webster et al. |
| 2013/0135609 A1 | 5/2013 | Gardner, Jr. et al. |
| 2013/0201469 A1 | 8/2013 | Treado et al. |
| 2014/0093147 A1 | 4/2014 | Stewart et al. |
| 2014/0171504 A1 | 6/2014 | Ganapathy |
| 2014/0231626 A1 | 8/2014 | Nelson et al. |
| 2014/0268104 A1 | 9/2014 | Treado et al. |
| 2015/0057530 A1 | 2/2015 | Roggeveen et al. |
| 2015/0133950 A1* | 5/2015 | Shelton ............ A61B 17/22012 606/128 |
| 2015/0216417 A1 | 8/2015 | Huang et al. |
| 2015/0297087 A1 | 10/2015 | Takamatsu et al. |
| 2017/0173275 A1* | 6/2017 | Anderson ............ A61M 25/065 |
| 2017/0224420 A1* | 8/2017 | Stringer ............ A61B 5/1459 |

FOREIGN PATENT DOCUMENTS

| | | | |
|---|---|---|---|
| WO | 1992014399 | 9/1992 | |
| WO | 1998000057 | 1/1998 | |
| WO | 1998005253 | 2/1998 | |
| WO | 2002057757 | 7/2002 | |
| WO | 2002096478 | 12/2002 | |
| WO | 2003087793 | 10/2003 | |
| WO | 2005034916 A1 | 4/2005 | |
| WO | 2006024479 A2 | 3/2006 | |
| WO | 2007014212 A1 | 2/2007 | |
| WO | 2010079222 A1 | 7/2010 | |
| WO | 2011100589 A1 | 8/2011 | |
| WO | 2012019102 A2 | 2/2012 | |
| WO | 2013056243 A1 | 4/2013 | |
| WO | WO-2013056243 A1 * | 4/2013 | ......... A61B 17/3401 |
| WO | 2013076216 A1 | 5/2013 | |
| WO | 2013119677 A1 | 8/2013 | |
| WO | 2014020156 A1 | 2/2014 | |
| WO | 2014143146 A1 | 9/2014 | |
| WO | 2015200712 A1 | 12/2015 | |

OTHER PUBLICATIONS

Lumileds Holding B.V., "High efficacy in a 3535 package with full range of CCTs and CRIs", DS203 Luxeon 3535L Line Product Datasheet, 2017, www.lumileds.com.

Rathmell et al., "Identification of the Epidural Space with Optical Spectroscopy—An In Vivo Swine Study", The American Society of Anesthesiologists, Inc., Dec. 2010, pp. 1406-1418, vol. 113, No. 6.

\* cited by examiner

LIGHT ASSISTED NEEDLE PLACEMENT SYSTEM AND METHOD

This disclosure is directed to the field of needle placement within the anatomy of a patient. It finds application, among others, in the placement of an epidural needle in the epidural space and supplements current methods of determining proper placement of a distal tip of the needle within the epidural space, although other uses of light to aid in a user's situational awareness are envisioned.

As an illustrative example, inserting needles into the epidural space of a patient is currently a blind procedure requiring significant practitioner experience detecting forces required to pass through various tissues layers, between vertebrae and into the epidural space. The "epidural space" is about a 2-8 mm space bounded by the relatively tough ligamentum flavum and the dural sac. Practitioners rely on haptic sensed indicators of arrival at the epidural space such as a change in the force experienced when a distal tip of the needle punctures the ligamentum flavum that occurs simultaneously with a "loss of resistance" to fluid flow from a syringe they are manipulating. As used herein, "haptic" means relating to or based on the sense of touch or tactile sensation, including but not limited to, the sensing of force as the distal tip of a needle advances through various tissues as well as the loss of resistance felt by a practitioner. Direct confirmation of proper placement can also be obtained, for example by injecting dye and obtaining a confirmatory X-ray.

Insertion of the tip of an epidural needle into the epidural space without perforation of the dural sac requires significant expertise and training. If the epidural needle is not advanced sufficiently past ligamentum flavum, the epidural space is not reached. Alternatively, if the tip of the needle is advanced too far, the dural sac may be punctured resulting in leakage of spinal fluid. If a puncture is recognized, typically anesthesia is converted from epidural anesthesia to spinal anesthesia. If the puncture goes unrecognized, severe complications arising from overdose or excessive anesthetic solution in the subdural space may result. Consequently anesthesiologists and other epidural injection practitioners have come to rely extensively on their training in palpating lumbar spinal structure and detecting various tissues by their haptic response to the needle's advance and to the simultaneous actuation of the plunger of a syringe filled with a fluid.

Light assisted needle placement systems, devices, kits, and methods described herein provide direct and objective real-time confirmation of the haptic sensations concurrent with the progression of the distal tip of a needle or other device through varying tissues encountered between the external skin layer, muscle, fat, bone, ligament and the like overlying the desired location within a patient and concurrent confirmation of entry of the needle into a desired location within the patient's body. In one example, devices and methods described here and are particularly useful for confirmation of entry of a needle into the epidural space. The light assisted needle placement system, when used to guide an epidural needle, may replace, but we intend its use to supplement the haptic responses currently used including the force to advance the needle, the loss of fluid flow resistance, the compliance of tissue to changes in fluid pressure and other current "touch and feel" methods, and as an indicator whether more time consuming methods such as injection of dye and confirmatory x-rays in epidural steroid injections (pain management procedure) may be necessary. Such systems and methods may enable other health providers to engage in the use of epidural steroid and other injections for treatment of neck, back, upper and lower extremity pain, increasing access to care.

The light detection device described herein, senses and provides visual concurrent confirmatory information to the practitioner and is able to detect both reflectance information about the tissue in which the tip of the needle is currently embedded as well as chromogen derive absorbance signals. These signals change in direct proportion to tissue and chromogenic changes as a function of: Needle tip movement; Light scatter from the granularity of the tissue; Chromogen concentrations in the tissue; Chromogenic changes in the fluid inside the needle; and Pressure changes induced by the plunger of the syringe barrel. While many of these signals are confounded at certain wavelengths and for similar tissues, there are sufficient differences between each tissue to enable positive identification of the transitions from one tissue type to another that correspond to concurrent haptic sensation and give reassuring confirmation of correct needle placement.

BRIEF DESCRIPTION OF THE DRAWINGS

FIGS. 9A-9E depict an example display representation of the progression of a tip of a needle to a desired location within a patient's anatomy.

DETAILED DESCRIPTION

Figure 1:
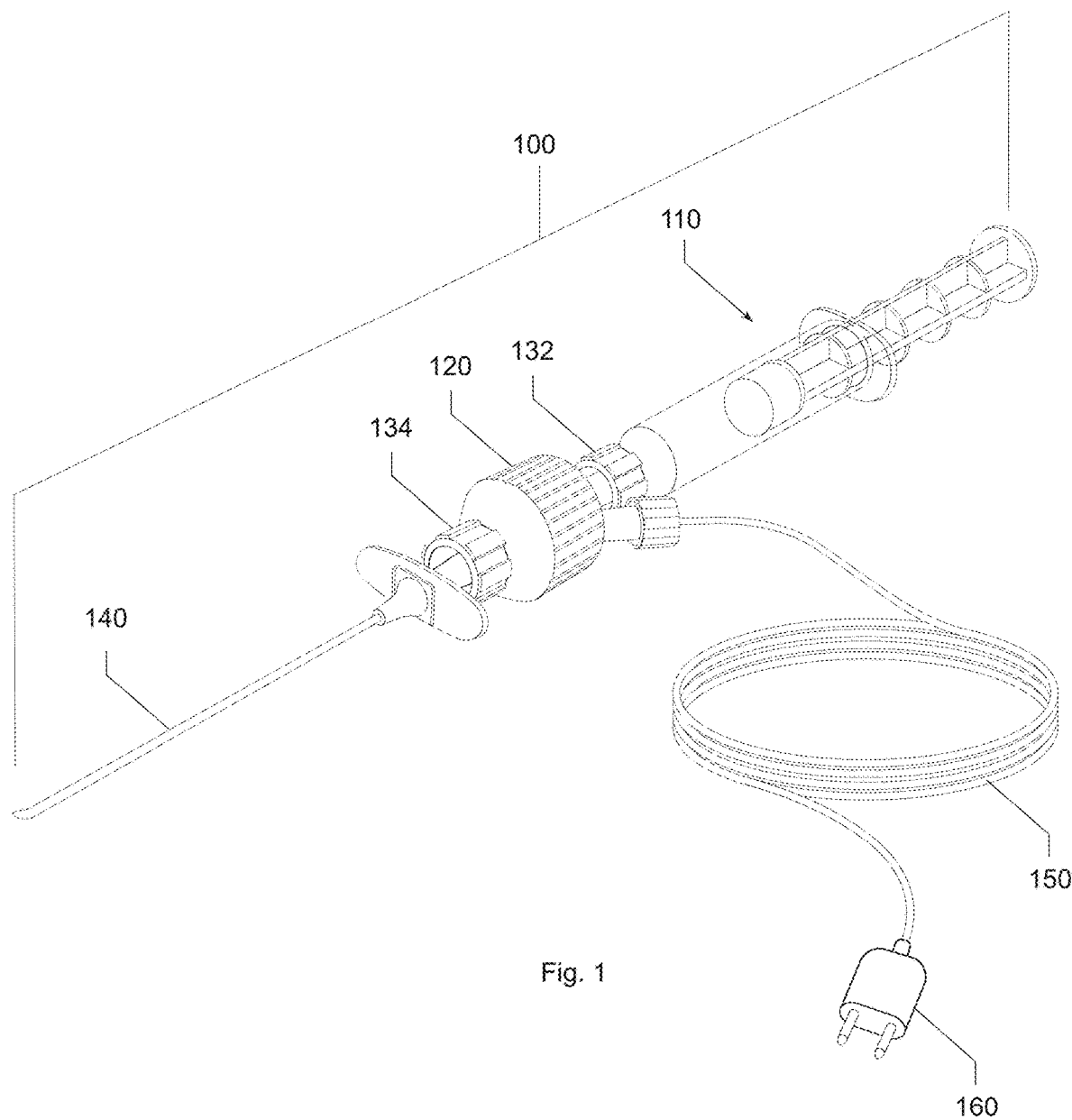
FIG. 1 is an exemplary view of an embodiment of a light assisted needle placement system.

A system, device, kit, and method are described herein to assist an operator of a device, typically a medical professional, in determining the location of a needle as it penetrates through tissues and into a desired site, such as positioning an epidural needle within the epidural space.

In one embodiment, a user connects a light coupling unit to a controllable fluid source, such as a fluid pump, syringe or the like on one side, and a needle, such as an epidural needle, on the other. The needle has a path for fluid communication therethrough between a distal sharp end and a proximal end connectable to the coupling unit.

The system contains a computing device including a processor programmed to control a light source, a light sensor, and a display unit. The processor analyzes returning light signals from a distal tip of the needle and displays the reflected luminance, the color and/or a representation of color at the distal tip. The processor additionally analyzes likely tissue transitions based on wavelength changes in returned light and includes the analysis on the display.

The devices described include a needle with the light coupling unit attached thereto, such that a path of fluid communication is provided from a syringe, through the coupling unit to the lumen of the needle, where optical paths, such as a single fiber or pair of fiber optic fibers extend to within a few millimeters of a distal tip of the needle. This enables the fluid from the syringe to provide haptic feedback to a user as well as an optical path for light pulses or signals from the light source via a fiber to a tissue plane and returns from the tissue plane to a fiber for detection by the light sensor and subsequent analysis and/or display by the processor.

The light source may be any collimated or non-collimated light, such as a light emitting diode (LED), incandescent light, and the like. The light source provides light of any desired wavelength, or multiple wavelengths. In embodiments, the light is a non-collimated light from LED or other non-collimated light producing device. Such a non-collimated source are generally and currently less expensive to implement than collimated light sources, such as lasers. However, coherent light sources may be substituted provided desired spectra or wavelengths can be obtained.

In one embodiment, light source is a low-power white-light broadband visible spectrum LED with a molded plastic lens. However, the light source may be chosen to enhance measurement of particular penetration tissues. Possible light source optical parameters include narrow or broadband spectral content from the UV to infrared region, linear or circular polarization, coherent or incoherent light, and intensity pulsing or modulation. These characteristics are readily available with off-the-shelf light sources, such as LEDs, laser diodes, incandescent bulbs, and discharge lamps, combined with the use of optional wavelength converting phosphors and optical filters. In addition suitable filters or wavelength sorting structures, such as gratings, may be employed to enable the illumination of the tissue at the tip of the needle with one wavelength while analysis is performed at a separate wavelength. This can enable the detection of fluorescent chromogens that might be present either naturally within a tissue or as an indicator within the light coupling fluid.

In embodiments, in order to eliminate the impact of ambient light on the measurement of reflected light intensity, two measurements are performed during each measurement cycle. First, the return light is measured with the LED off (i.e., only ambient light is measured). Then the returned light is measured with the LED on (i.e., a sum of ambient light and the true return light is measured). Subsequently the results are subtracted, either electronically or by the logic unit, one from another yielding the intensity value of returning light signals.

The measurements may be performed continuously. By way of example, light measurements may be taken every 500 μs, i.e., true return light measurements are obtained every 1 ms (1 kHz frequency). The results are accumulated, and preferably the result is box car averaged at regular intervals (e.g. every 50 ms or other suitable interval). Averaging is implemented to reduce the level of noise in the measurement.

Following proper insertion in a patient, the needle may be used to provide epidural anesthesia; epidural steroid injections, such as for treatment of back pain. The needle may also be used to insert a catheter for continuous infusion of an analgesic to maintain pain relief at a predetermined location during a procedure such as the pudendal region during child birth. Alternatively the needle guidance system may be used to insert a device, such as electrical stimulator leads, into the epidural sp ace.

In other embodiments, the needle guidance system described herein may be configured to be suitable to guide orthopedic, neurosurgical or surgical piercing instruments. In yet a further embodiment, the guidance system may be configured to be used in non-medical piercing and/or perforating equipment.

Referring now to FIG. 1, an embodiment of a partial light assisted needle placement system 100 is depicted. The system 100 includes a controllable fluid source, such as syringe 110, preferably filled or fillable with a fluid, such as sterile saline solution although other gaseous or liquid phase fluids may be substituted by certain users or in other applications. The syringe is connectable to a light coupling unit 120 on a first side via a Luer lock 132 or other suitable attachment mechanism. The light coupling unit 120 is also connectable on a second side to an epidural needle 140, such as a Tuohy needle via a second Luer lock 134 or other suitable attachment.

In connected form, a path for fluid communication is provided between the syringe 110, through the light coupling unit 120 and needle 140. In one embodiment, when a user depresses the syringe plunger, saline will fill an interior volume of the coupling unit and the needle will fill with saline until the fluid is ejected from the opening at the distal end. This enables experienced epidural providers to receive the same "loss of resistance" feedback they experience with more conventional methods. Additionally, as further discussed below, the saline filled coupling unit 120 and needle 140 provide an optical path from an end of light transmission media such as optical fiber or lens to a distal tip of the needle 140. This permits the fluid to act: As a vehicle to provide haptic fluid flow resistance feedback during a needle placement procedure; As a vehicle to transmit reflected light from a light scattering surface or tissue or light absorbing chromogen within a tissue; and As a vehicle to provide absorbing chromogen dye(s) which may be used to mark the transition from a solid reflecting surface and a fluid passing channel. In one particular instance, upon entry of the tip of needle into the epidural space, the fluid transmits both the haptic response of the loss of resistance of fluid flow and loss of reflectance to the user.

Figures 2, 3:
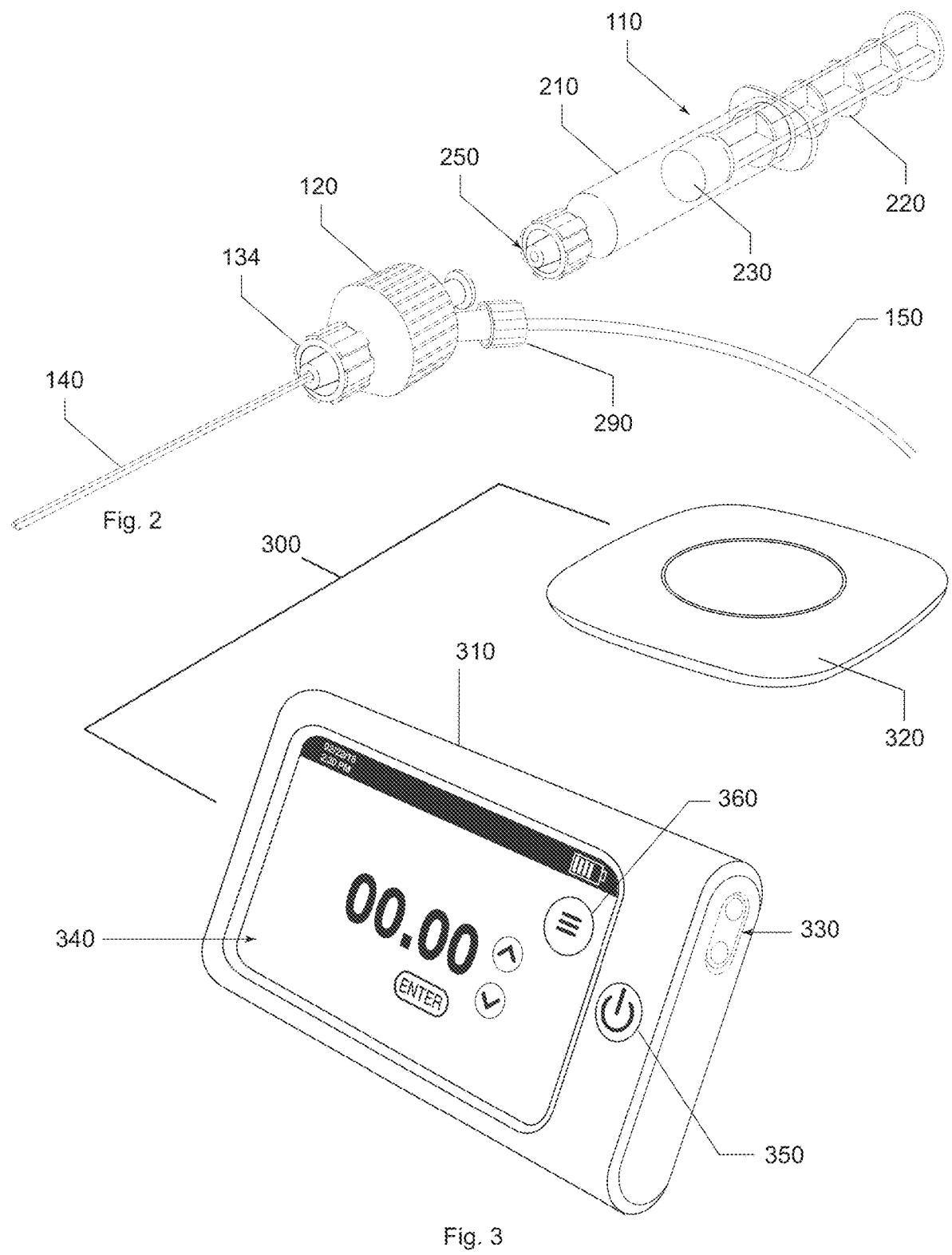
FIG. 2 is an enlarged view of separated components of a light assisted needle placement system.
FIG. 3 is a perspective view of a controller and charging component of a light assisted needle placement system.

As more completely discussed below, the system 100 also includes a connecting cable 150 to establish a path for data communication between the coupling unit 120 and a separate controller (FIG. 2). The data can include electrical signals, optical signals or both. The connection may also be wireless in certain embodiments.

With reference now to FIG. 2, syringe 110 may include a conventional medical grade plastic or glass body 210 defining an interior volume through which plunger 220 and actuator 230 cooperate to either expel fluid from or suction fluid into the volume at tip 250. The syringe 110 mechanically connects, for example by a Luer lock or slip tip, onto a proximal side of the coupling unit 120, which in turn, mechanically connects on a distal side 260 to a needle (not shown).

Referring now to FIG. 3, a controller package 300 includes a control panel 310 and a wireless charger 320. The panel includes a connector 330 to accept the connecting cable 150 terminal end 160 (FIG. 1). The control panel 310 includes a display 340 to provide a user with data processed by a computing device either in the controller or in the coupling unit 120, where displayed data includes: amount of light returned; visualizations of where in the patient's anatomy the distal tip of the epidural needle is or may be; color coding indicating acceptability of the current position; (i.e. "green" is positive indication of correct final location in the epidural space); an estimate of the type of tissue; and/or color returned of reflectance signal currently at the distal end of the needle. For example, skin, muscle, fat, tendon and epidural space have differing light returns (where return can indicate reflection, scatter, absorbance, fluorescence, or loss of reflectance among others) and these returns can be provided directly to the user and/or processed to provide additional situational awareness to the user. In one embodiment, the processing, light source, and light sensor are all disposed within the control panel 310, but optionally select features may be alternately disposed within the coupling unit 120 itself.

The display 340 provides a visual indication to replace or supplement the user's experience. For example, the sudden change in force required to advance the needle, and/or the loss of resistance to fluid flow felt on the plunger when the epidural space is encountered, can be confirmed by reference to the display where visual data is simultaneously displayed showing a loss in the reflectance signal or a sudden change in the color that matches the detected change in reflectance or spectrum to exactly match a medical professionals expectation. The control panel additionally includes functional controls such as a power button 350 and a menu button 360 and/or a touch screen overlaid on the display screen 340 to enable user control and selection of display modes, operation modes, programming modes, display units and other desired features.

For example, a user connects a first side of the light coupling unit to a syringe and a second side of the light coupling unit to an epidural needle. This establishes a path of fluid communication from the syringe, through the light coupling unit and to the epidural needle. In use, it also establishes an optical coupling between the source of light provided either to the coupling unit or to a distal end of fibers disposed in the needle. A user may then connect the connecting cable from the coupling unit to the control panel and power the device on and select monitoring options. As part of the start-up procedure with each new coupling unit, the user may advance the tip of the needle into at least one of a variety of reflectance standards to provide calibration signals back to the controller. Continuing, the user may next insert the epidural needle into a patient and monitor progression of the needle to the epidural space both via haptic detection of the change in force required to advance the needle, the haptic response felt by the resistance to fluid flow felt on the syringe plunger and via reference to the visual display where tissue granularity (light scatter reflectance) and tissue color (chromogen absorbance) and tissue compliance (changes to reflectance observed every time the syringe plunger is pressed) at the distal tip can be seen. The user continues until a sudden change in the force required to advance the needle is felt, and/or the loss of resistance to fluid flow or other conventional feedback is received indicating penetration of the epidural space and then simultaneously confirmed by reference to the visual display showing a loss of reflectance signal and a sudden change in the color of the desired placement of the epidural needle. The user may then disconnect the light coupling unit from the epidural needle, thread a catheter into the epidural needle and provide anesthetic conventionally to the epidural space.

Figure 4:
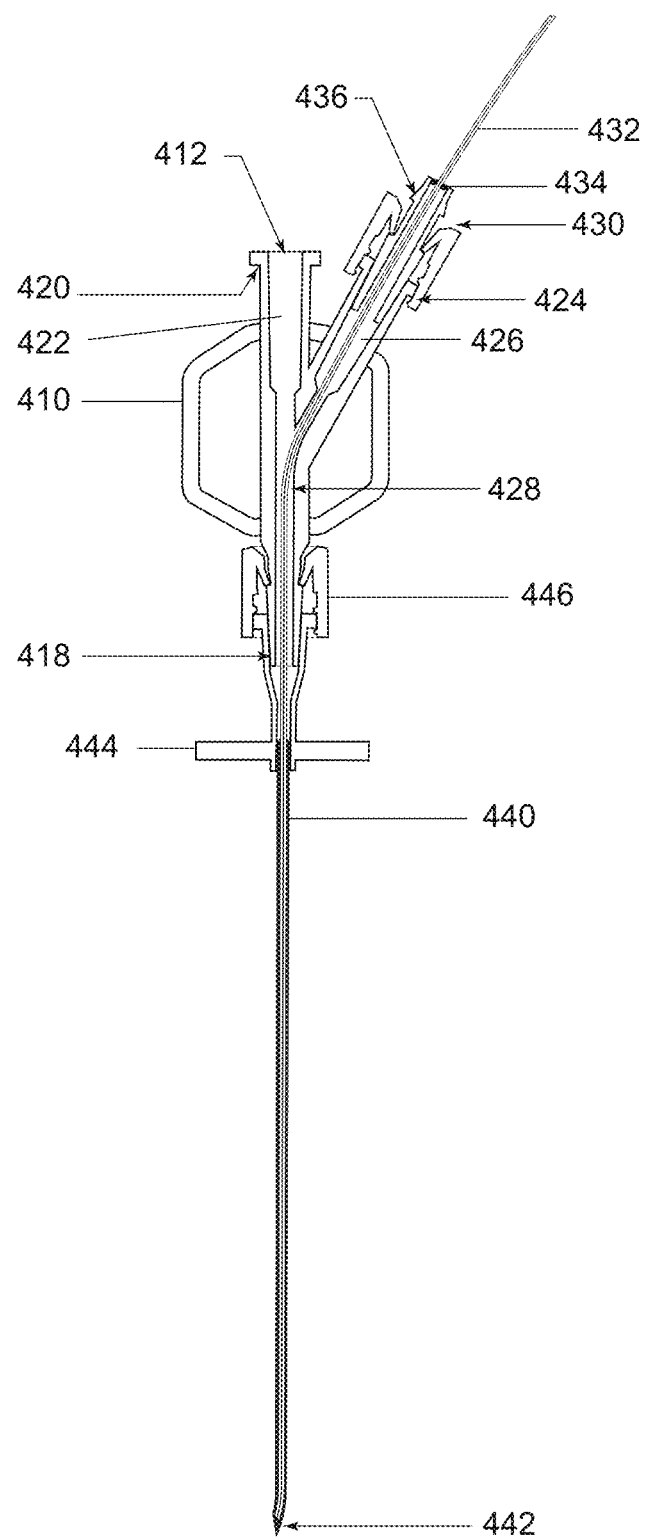
FIG. 4 is a cross sectional view of another embodiment of a light assisted needle placement system.

Referring now to FIG. 4, aspects of an alternate embodiment of a needle guidance system 400 is shown in cross section. The system 400 includes a coupling unit 410 having a proximal end 412 and an opposed distal end 418. The proximal end 412 includes a syringe connection point 420, configured to mechanically attach to a syringe (not shown). The syringe connection point 420 defines a beginning of a first channel 422 for fluid communication into and through the coupling unit 410. The proximal end 412 also includes a fiber connection point 424 defining a second channel 426 intersecting the first channel 422 at an angle. The distal end 418 surrounds the first channel 422 on a distal side 428 of the intersection of the first channel 422 and the second channel 426. In use, a user connects a fiber assembly 430 including a fiber pair 432 epoxied 434 or glued into a barb tube 436 configured to mechanically connect with the fiber connection point 424. The user additionally connects an epidural needle 440, such as a Tuohy needle, to distal end 418 of the coupling unit 410. The fiber pair 432 is provided at a length to permit connection to a controller (not shown) on a proximal side and to terminate a short distance from a distal tip 442 of the needle as further discussed below. Tabs 444 may be provided to provide the user with close haptic sensing of the force required to advance the needle. Luer locking rings 446 may be provided to assure leak free sterile connection during any procedure that creates significant pressure within the fluid coupling space.

Figure 5:
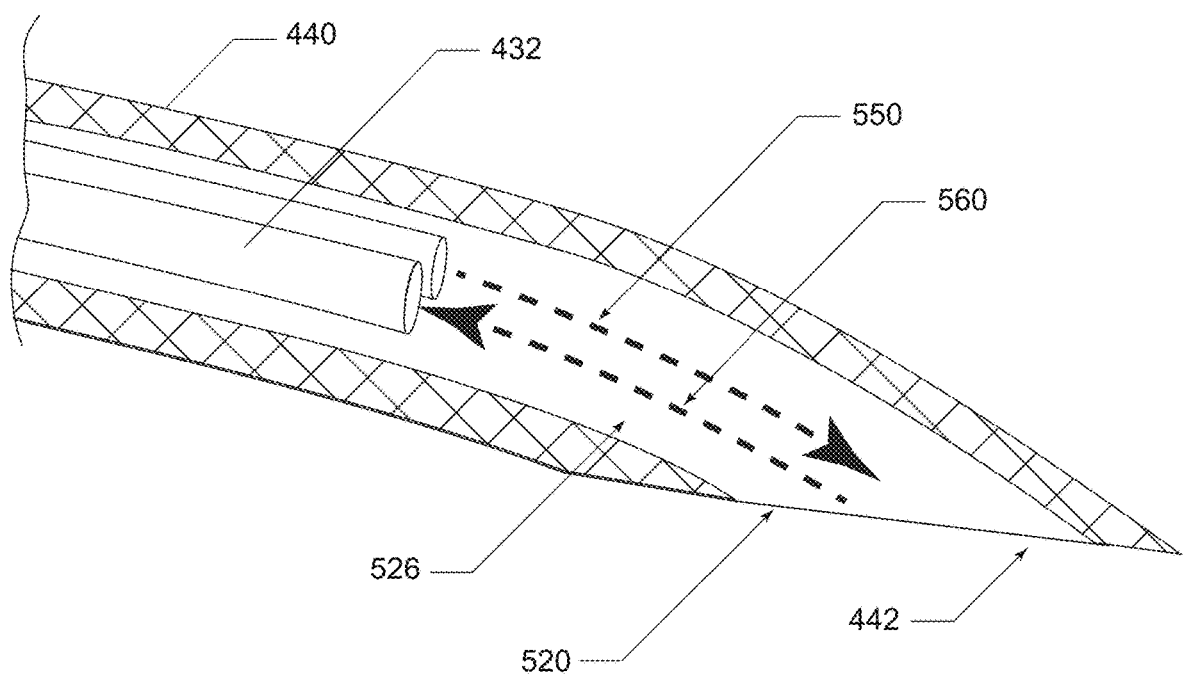
FIG. 5 is a detail of the distal end of the light assisted needle placement system of FIG. 4.

Referring now to FIG. 5, a detail of the distal tip 442 of the needle 440 is illustrated. As can be seen, the fiber pair 432 is preferably oriented in a "side-by-side" arrangement within the needle 440, but not entirely filling the fluid channel within the needle. In other words, space exists to permit fluid communication between the syringe (not shown) and the distal tip 442. One of the fiber pair connect on a proximal side to a light source, preferably a source generating white, or red, green and blue light. The other fiber pair connects on the proximal side to an optical sensor, such as a photo diode. In alternate embodiments, a single fiber may connect to both a light source and a light sensor via a splitter or other optical means, where the illuminating light from the light source is pulsed such that returning reflected light signals from pulses may be returned on the single fiber for detection by the optical sensor. The fluid may be clear for transmitting only the light scattered, reflected or absorbed by tissues, or lost into non-reflecting epidural spaces. Alternatively at least one portion of the fluid my contain a predetermined biocompatible dye, such as blue (Anthocyanin, Indigotine) or green (FD&C Green No. 2, No. 3) food coloring or a fluorescent dye. When a small portion of a dye is utilized at the distal tip of the needle followed by a transparent fluid more proximal to it, the dye can be used to indicate that dilution has occurred such as when the tip reaches and opens into a cavity such as the epidural space. This arrangement of fluids with different chromogenic aborbances, that are detected and referenced by the logic unit, can also therefore be used to indicate the presence of a solid coring plug that has become lodged into the tip, or the presence of blood preventing sufficient reflectance signal.

On the distal side, the fiber pair 432 terminates a short distance from a plane 520 defining the opening of the distal tip 436. In use, this plane 520 is a tissue plane that deflects between concave and convex depending on pressure applied by the user urging fluid from the syringe to the distal tip of the needle 440. The distance between the terminal end of the fiber pair 432 and the plane 520 may range between 1 mm and 18 mm, preferably between 3 mm and 10 mm, more preferably between 4 and 7 mm.

With continued reference to FIG. 5, in use, illuminating light 550 from a light source (not shown) travels down one fiber of the fiber pair 432, and to the plane 520 through a fluid 526, for example, saline, in the needle 440. The illuminating light 550 is partially reflected and/or scattered by the plane 520 and the reflected and/or scattered light 560 travels back through the fluid filled needle 440 and into the other fiber in the fiber pair 432 that terminates in an optical sensor (not shown) as discussed above. The terminal end of the fiber pair 432 is slightly distanced from the plane 520. Accordingly, light travels from the fiber pair 432 to the fluid 526 in contact with the tissue plane 520 and is reflected back to the fiber pair. This is believed to provide a mechanism to obtain relatively consistent light interactions between the light source and sensing mechanisms on the one side and the tissue plane 520 on the other. The consistent interactions benefit from the terminal ends of the fiber pair 432 normally being spaced from the tissue. This is in contrast to a fiber pair terminating at the distal end 442 of the needle where they would be in contact with the tissue in some circumstances when, for example, the tissue is at or within the distal end, and spaced from the tissue in others when, for example, the user applies pressure on the syringe plunger or withdraws the needle.

In that regard, we have discovered that there are at least five sources of returning light signal. One source is from the tissue plane itself. The tissues absorb and reflect light depending on spectra of chromogens within the tissues themselves. This is a component in identifying the tissue type as more completely discussed below. A second source is light scatter. This can also be a component in identifying tissue as light scatter appears to be proportional to tissue granularity or the changes in index of refraction associated with the cell membranes and intracellular structures. A third source depends of the presentation of the tissue plane. Specifically, if the tissue plane is bowing into (convex) the tip of the needle, or if it is flat, or if it is bowing out (concave) of the tip. The presentation of the tissue plane changes the angles of transmission and reflection and thus changes the signal strength. A fourth source may be the relative reflected absorbance of a dye within the transmitting fluid. This signal will be most pronounced when the tissue plane is a highly scattering surface of broad spectrum light such as the white ligamentum flavum. In such a situation, the dye's signal intensity is directly propotional to the length of the light path that it is traveling through. And a fifth source of signal of the returning light may be the absence of any reflecting or absorbing surface at the flat plane that defines the needle tip opening. This is a typical condition that may be experienced when the tip of the needle emerges into a fluid conducting space such as the epidural space. As noted above, once in the epidural space, there is no or very little reflection, while saline from the syringe fills the epidural space surrounding the tip of the needle.

Figure 6:
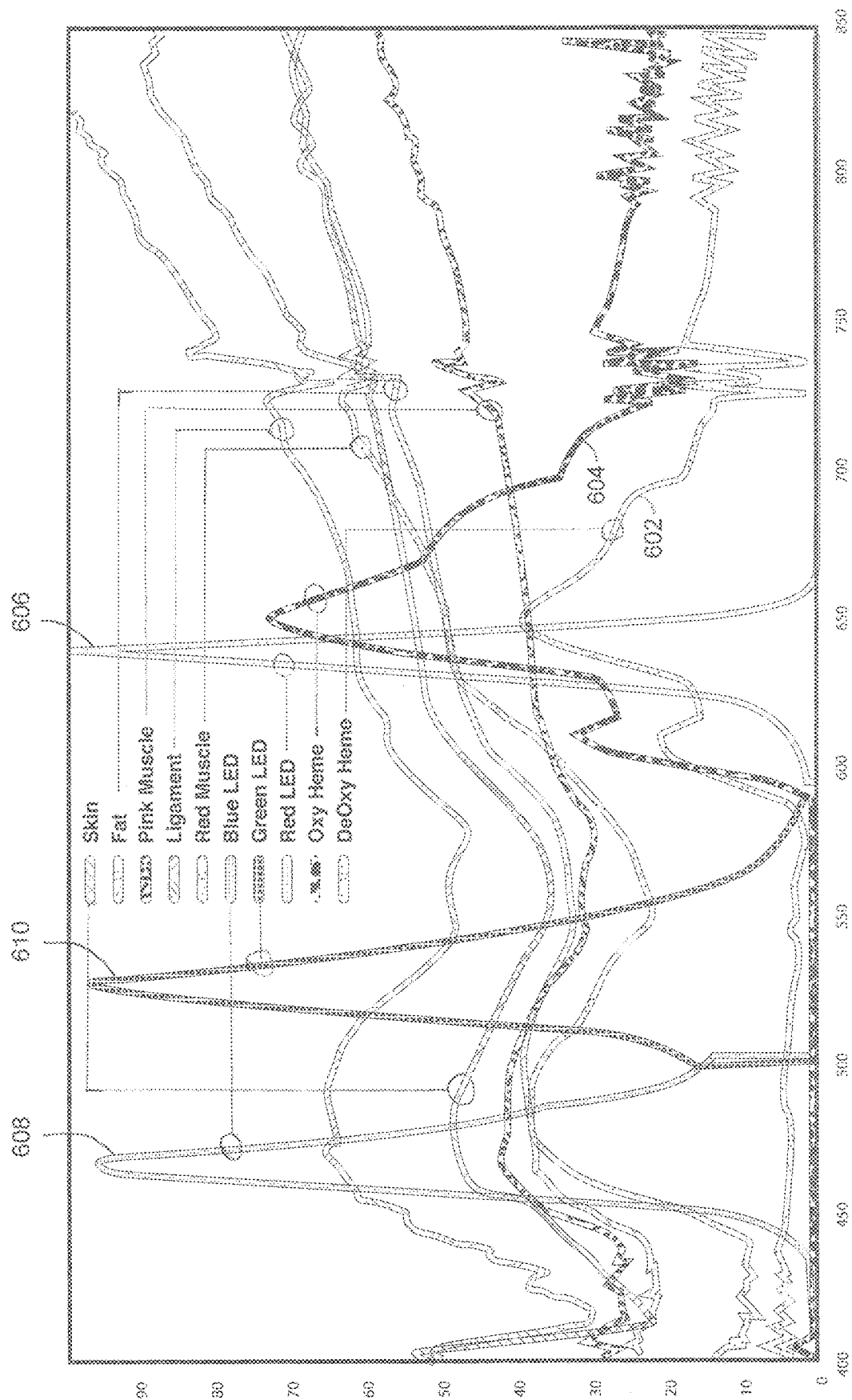
FIG. 6 is a graph showing the spectra of various tissue types as detected through the fiber optics of a needle guidance system.

With reference now to FIG. 6, a graph shows spectral response of various tissue types. For example, both deoxy heme 602 and oxy heme 604 curves respond well in the vicinity of "red" 606 and are nearly absent at "blue" 608 and "green" 610. Analysis of the wavelength response for each tissue allows a processor to detect transitions between tissue types and provide an indication to a user. Such transitions are useful to confirm user feel upon transitioning from a primarily fatty tissue having a first spectral response to muscle tissue having a second spectral response and again upon encountering ligamentous tissue having a third spectral response. Similarly, analysis of spectral response may allow a processor or look up table to provide an estimate of the tissue type present at the distal end of the needle that may be presented to a user as an additional indication of anatomical location. Additionally, a color indication at the distal tip of the needle can be displayed to supplement the feel of the needle advancing through transitional tissue layers toward the epidural space or other desired location. Such additional data can allow a user to anticipate the loss of force required to advance the needle and the "loss of resistance" to fluid flow before and immediately after it has occurred preventing inadvertent penetration of the dural sac.

Figure 7:
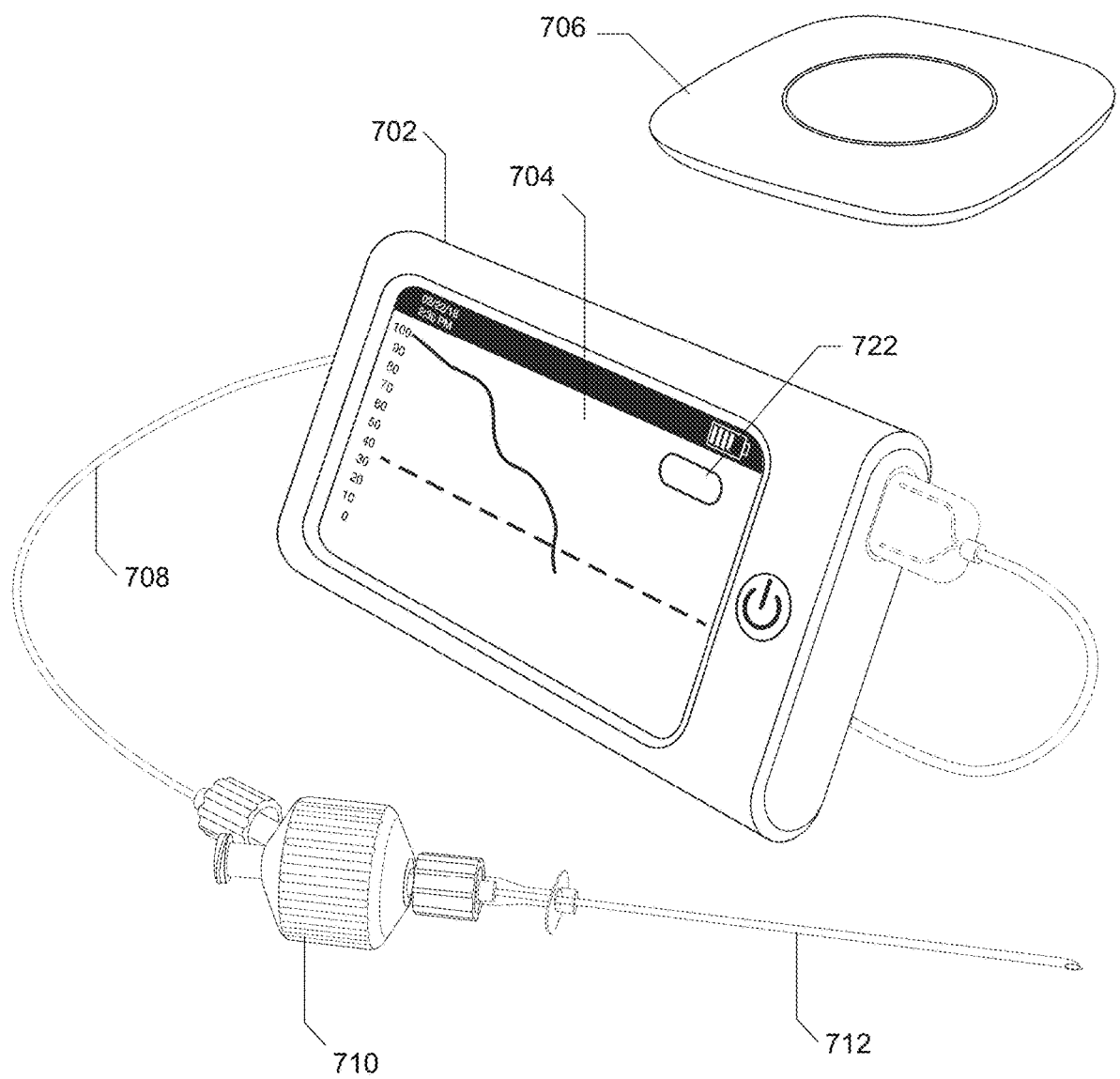
FIG. 7 is a needle guidance kit with attached needle.
Figure 8:
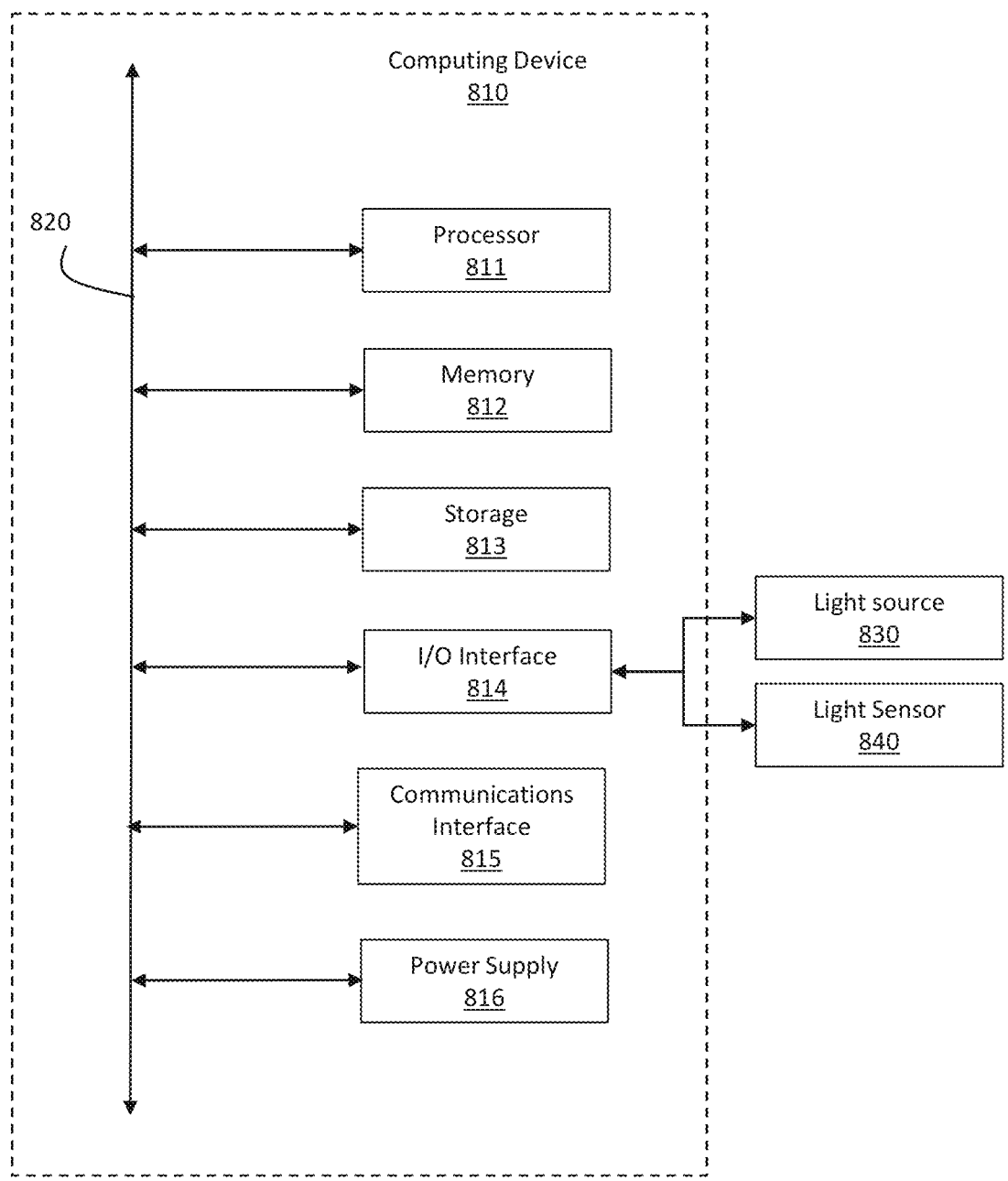
FIG. 8 is a block diagram depicting an example hardware implementation.

Referring now to FIG. 7, a light assisted needle placement kit may include a housing 702 containing a display 704 and components of the electrical and optical sources and sensors discussed above and for example, the parts or entirety shown in FIG. 8 below. The kit may also include a charger 706, battery or other power supply, an optical and/or electrical connector 708 and a light assisted needle placement system 710 shown with a needle 712 connected, although kits may alternately exclude needles allowing users to select appropriate sizes depending on use. The display 704 includes a window 722 that provides a real-time, color image of the tissue plane encountered by the distal tip of the needle. Instead of a single interpretation of the color, the processing unit can also continuously graph each individual time dependent signal derived from each LED. Or in the case of the use of a white light LED source and a miniature spectrometer such as might be provided by the Hamamatsu Corporation, the processor might provide the graph of a complete spectrum changing or a 3 dimensional plot of the surface showing the time-dependent spectra. This can assist the user in identifying a particular anatomical location and show transitions between different tissues. Additionally, the display can display a continuously running graph or other indication of the time-dependent luminance response encountered at a particular location.

Any suitable computing system or group of computing systems can be used to implement the techniques and methods disclosed herein. For example, FIG. 8 is a block diagram depicting one exemplary implementation of such components. A computing device 810 can include a processor 811 that is communicatively coupled to a memory 812 and that executes computer-executable program code and/or accesses information stored in memory 812. The processor 811 may comprise a microprocessor, an application-specific integrated circuit ("ASIC"), a state machine, or other processing device. The processor 811 can include one processing device or more than one processing device. Such a processor can include or may be in communication with a computer-readable medium, including but not limited to memory 812, storing instructions that, when executed by the processor 811, cause the processor to perform the operations described herein. For example, processor 811 includes control logic or is programmed to control the light source and sensor and analyze the returning light signals received by at least the light sensor 840, and to provide output regarding color at the distal tip, system status, and tissue transition information, when the appropriate conditions are reached.

The memory 812 can include any suitable non-transitory computer-readable medium. The computer-readable medium can include any electronic, optical, magnetic, or other storage device capable of providing a processor with computer-readable instructions or other program code. Non-limiting examples of a computer-readable medium include a magnetic disk, memory chip, ROM, RAM, an ASIC, a configured processor, optical storage, magnetic tape or other magnetic storage, or any other medium from which a computer processor can read instructions. The instructions may include processor-specific instructions generated by a compiler and/or an interpreter from code written in any suitable computer-programming language, including, for example, C, C++, C#, Visual Basic, Java, Python, Perl, JavaScript, and ActionScript.

The computing device 810 executes program code that configures the processor 811 to perform one or more of the operations described above. Specifically, and without limitation, the program code can include code to configure the processor to provide the functionality described herein including controlling the light source, light sensor, and frequency analysis. The program code may be resident in the memory 812 or any suitable computer-readable medium and may be executed by the processor 811 or any other suitable processor. In some embodiments, modules can be resident in the memory 812. In additional or alternative embodiments, one or more modules can be resident in a memory that is accessible via a data network, such as a memory accessible to a cloud service.

The computing device 810 may also comprise a number of external or internal devices such as input or output devices. For example, the computing device is shown with an input/output ("I/O") interface 814 that can receive input from input devices or provide output to output devices. Specifically, I/O interface 814 communicates with light source 830 controlling pulse sequences, frequencies and lighting as described herein. Similarly, I/O interface 814 communicates with light sensor 840 receiving returning light signals as described. In another example, a graphical user interface, display, or the like can be suitably driven by the I/O interface 814.

The light source 830 and light sensor 840 may each powered by a power supply 816, individual power sources or the processor 811.

The light source 830 may be pulsed or modulated by a digital or analog control signal from processor 811. Preferably the light source is a compact electrically driven light source emitting adequate radiant flux to allow measurements by the light sensor. One embodiment provides a three pulse sequence, for example, a red pulse, followed by a green pulse, followed by a blue pulse, each of these separated by a period when no light is transmitted to enable measurement of background ambient light leaking into the measurements. We have observed, for example that the individual R returns, G returns and B returns usually follow each other in a coincident manner proportional to the granularity of each tissue and its relative reflectivity. However they also diverge in non-coincidence at specific tissue layers as the color of each tissue changes, for example from yellow-ish white at fatty layers to dark red at muscle layers to grey-ish white at ligament layers.

Light sensor 840 is configured to receive reflected light signals from the optical fiber and convert the reflected light to an electrical signal. The light sensor may be spectrally matched to the light source 830 and may be sensitive to optical wavelengths of interest. The response time is selected to be adequate to detect light intensity variations during penetration of different tissues or spaces in a patient's body by the distal end of the needle to determine when the distal tip reaches the desired site.

An example of a suitable light sensor is a photodiode with a molded plastic lens. Other suitable light sensors may be selected based on cost, sensitivity, and response time. Alternative suitable light sensors include a light dependent resistor, photovoltaic cell, phototransistor, CCD, microbolometer, photomultiplier tube, spectrometer photodiode array, or other electro-optical sensor matched to the light source.

Optionally, optical filters may be applied to the light sensor to restrict the measurement spectrum or polarization, to reduce interference, or increase measurement sensitivity. The light sensor may contain a lens for efficient optical coupling between the optical fiber and light sensor.

A communication interface 815 may also be included in the computing device 810 and can include any device or group of devices suitable for establishing a wired or wireless data connection to one or more data networks. Non-limiting examples of the communication interface 815 include an Ethernet network adapter, a modem, and/or the like. The computing device 810 can transmit messages as electronic or optical signals via the interface 814.

Computing device 810 may also include a power supply 816 adapted to supply suitable power to the needed components including those discussed herein. The power source 816 for the computing device 810 may include an internal battery or an external power source or charger. In one embodiment, the assembly uses an internal battery, although power may be provided through an external power jack that overrides internal battery power, on-board energy storage in the form of a rechargeable or non-rechargeable battery or other energy storage device, with control of energy management may be performed by processor 811. Power may be supplied to components using electrically conductive wires, wireless power transfer using inductive, RF, or optical power transfer, or other methods.

A data bus 820 can also be included to communicatively couple one or more components of the computing device 810.

Figure 9A:
Figure 9B:
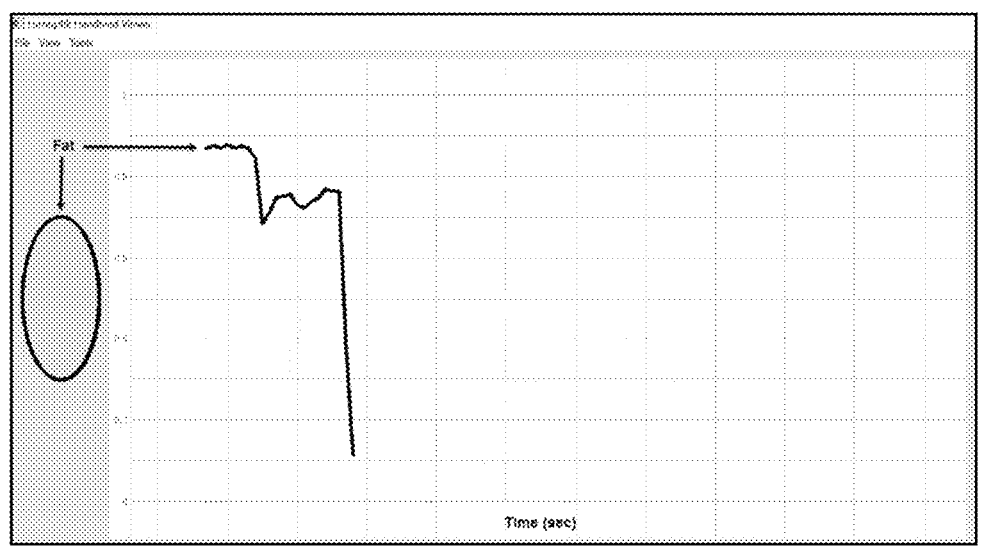
Figure 9C:
Figure 9B:
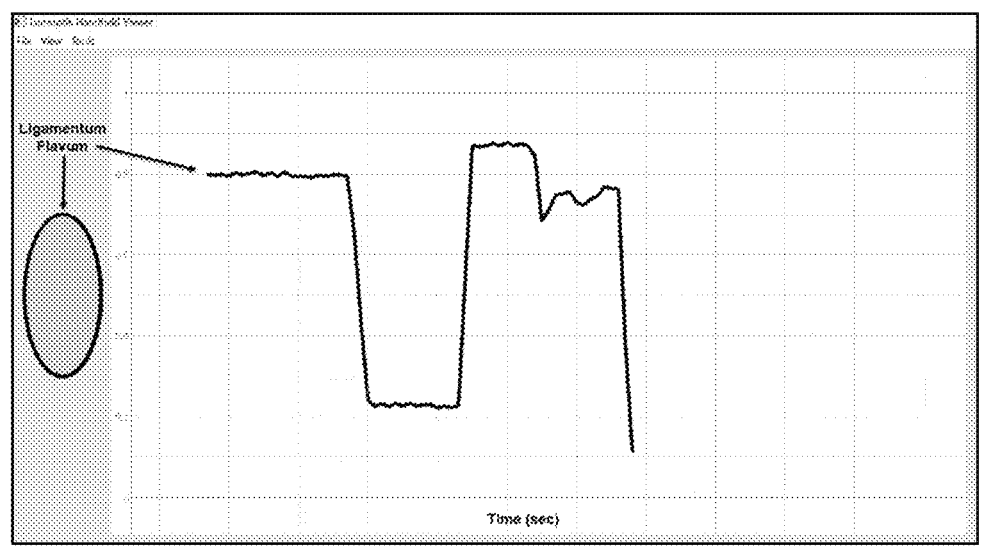

Referring to FIGS. 9A-9E one can see a time sequence illustration of both the tissue reflectivity and tissue color changes that might typically be displayed on the computing device display as a medical professional advances an epidural needle through various tissues during a typical epidural procedure. Starting in FIG. 9A the needle is advanced from outside the body where a droplet of saline is present on the tip of the needle into a pink skin layer. The strip chart recording illustrates the reflected "luminance" signal starting at near zero, when only a droplet of saline is present and virtually all of the light transmitted to the tip for all 3 colors is lost (none is reflected back), to a state where approximately 75% of the light is reflected back and the color oval to the left of the strip chart is filled in with a pinkish color that is the equivalent of the color determined by the RGB measured reflectance signals. This then progresses to FIG. 9B as the needle progresses deeper into the tissue where the reflected signal increases to approximately 87% and the color filling in the oval shows a yellowish-white indicating that the tip of the needle is now in fat. Then, as illustrated in FIG. 9C, when the needle penetrates further, one will see the reflectance drop significantly to a range of luminance values around approximately 30% and the color within the oval shows a dark reddish or maroon color, when the tip of the needle penetrates a muscle. And again, as illustrated in FIG. 9D, when the needle penetrates further into a tendon or ligament, such as the ligamentum flavum, one typically might see the overall luminance signal rise to from 70% to 90% reflectance, and the color within the oval will show a bright white to greyish-white color.

Figure 9E:
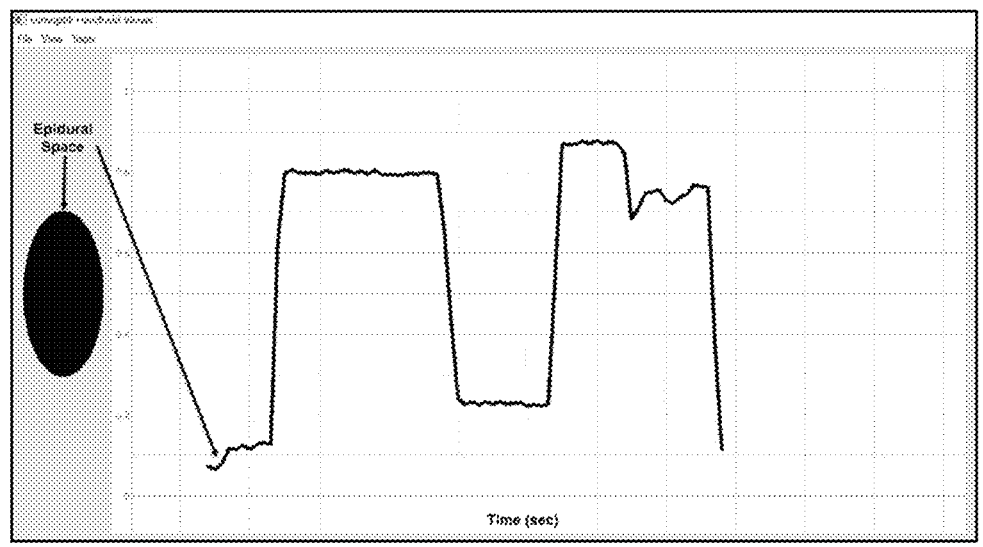

At this point the medical professional will encounter significant resistance to advancing the needle forward and must increase the force exerted on the needle until they feel sudden loss of the force required. In addition, if they are pressing on the plunger of the syringe, they will experience significant back pressure against the plunger, until the needle tip breaks through the ligamentum flavum. Whereupon, they will feel a sudden loss of resistance to both forward motion, and fluid flow from the syringe. At this point they will also visually observe what is shown in FIG. 9E. The overall reflectance signal will suddenly decrease to near zero and the color within the oval will be very dark, in some cases even black.

As noted, the light assisted needle placement system may be provided in kit form. Minimally, a kit may include a light coupling unit 120, 410, 710; a control panel and/or housing 310, 702; connector or connecting cable, 150, 432, 708 and a suitable power source such as charger, 320, 706. The individual components may all or selected ones by provided as sterile, self-contained disposable devices or in reusable form. Further, the light assisted needle placement system may be provided in sterile packaging with the system fully or partially preassembled (i.e. connecting cable pre-measured and affixed to the light coupling unit) and ready for connection with conventional needles and/or fluid sources. Alternately, the kit may be completely self-contained including all needed components to place a needle within a desired body space. Preferably the kit contains instructions to guide the user in proper assembly, use and optionally disposal, of the light assisted needle placement system, for example, instructions detailing use in connection with the combination of one or more haptic feedback sources and visual confirmation of tissue transitions and arrival of the distal tip of a needle at a desired body space, or as otherwise described herein.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure the claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

The invention claimed is:

1. A method for detecting a coring plug in an epidural needle during an epidural procedure, the method comprising:
  connecting a first side of a light coupling unit to a controllable fluid source having a plunger movable within a volume to advance fluid from the fluid source through the light coupling unit;
  connecting a second side of the light coupling unit to the epidural needle establishing a path of fluid communication from the fluid source, through the light coupling unit and into a lumen through the epidural needle;
  establishing a first path of optical signal communication from a light source to the path of fluid communication, where a terminal end of the first path of optical signal communication is located between 3 mm and 10 mm from a distal tip of the epidural needle;
  establishing a second path of optical signal communication from a distal tip of the epidural needle through fluid in the lumen to the terminal end of the first path;
  detecting returning light signals from the distal tip of the epidural needle at a light sensor;
  displaying a depiction of the returning light signals at the distal tip of the epidural needle; and
  detecting a coring plug that has become lodged into the distal tip by noting lack of change in reflected light.

2. The method as set forth in claim 1 further comprising powering the light source in optical communication with the first path of optical signal communication.

3. The method as set forth in claim 1, where the fluid source comprises a syringe.

4. The method as set forth in claim 3, where the fluid comprises saline, the method further comprising advancing saline from the syringe through the path of fluid communication to provide for transmitting light.

5. The method as set forth in claim 1, further comprising analyzing returning light signals and displaying an indication of a tissue transition at the distal tip of the epidural needle based on wavelength of the returning light signals.

6. The method as set forth in claim 1, where the depiction of reflected light comprises a color corresponding to the reflected light.

7. The method as set forth in claim 1, where the displaying comprises continuously providing a running indication of time-dependent luminance response at the tip of the epidural needle.

8. A machine to detect a coring plug during an epidural procedure, the machine comprising:
  a light coupling unit having first and second connectors, where the first connector connects the light coupling unit to a syringe and where the second connector connects the light coupling unit to the needle, where, when so connected, a path of fluid communication is established between the syringe, through the light coupling unit to a distal tip of the needle, the light coupling unit further having a connection for an optical cable including:
    a first path of optical signal communication from a light source to the path of fluid communication, where a terminal end of the first path is disposed between 3 mm and 10 mm from a distal tip of the needle, and a second path of optical signal communication separate from the first path, where the second path communicates reflected light to a light sensor and where a terminal end of the second path is disposed adjacent to the terminal end of the first path;

a third path of optical signal communication separate from, but in optical communication with the first and second paths of optical signal communication, the third path comprising fluid in the needle between the distal tip of the needle and the terminal ends of the first and second paths of optical signal communication;

a controller including: the light source that selectively provides light along the first path of optical signal communication; the light sensor that receives reflected light from a distal end of the needle; and a display displaying a reflected light representation of a tissue plane at the distal tip of the needle, where following needle insertion the display provides depictions of transitions from a tissue type based on changes in the reflected light representation, where lack of changes in the reflected light representation indicate presence of a coring plug that has become lodged into the distal tip.

9. The machine as set forth in claim 8, further comprising a power source suitable to power the machine.

10. The machine as set forth in claim 8, further comprising the syringe.

11. The machine as set forth in claim 8, where the fluid comprises sterile saline.

12. A method for detecting a coring plug during an epidural procedure, the method comprising:

attaching a fluid source to a first side of a light coupling unit;

attaching an optical pathway to the first side of the light coupling unit;

threading the optical pathway through a lumen of an epidural needle;

attaching the epidural needle to a second side of the light coupling unit;

inserting the epidural needle into tissue of a patient;

filling the lumen with fluid from the fluid source;

providing a light along the optical pathway and exiting the optical pathway axially within the lumen, where the light continues to a distal tip of the epidural needle through the fluid in the lumen;

displaying a depiction of reflectance of the light illuminating a tissue plane at the distal tip of the epidural needle; and detecting a coring plug that has become lodged into the distal tip by noting lack of change in the depiction of reflectance.

13. The method as set forth in claim 12, further comprising:

causing light to travel along a first path of optical signal communication from a light source, through the optical pathway, to a terminal end of the first path disposed between 3 mm and 10 mm from the distal tip of the needle, where the light exits the first path and enters into the fluid filling the lumen of the epidural needle to the tissue plane, and detecting reflected light from the tissue plane.

14. The method as set forth in claim 12, further comprising:

analyzing reflected light from the tissue plane; and displaying an indication of a tissue transition at the distal tip of the epidural needle based on frequencies of the reflected light signals.

\* \* \* \* \*